(12) United States Patent
Savin

(10) Patent No.: US 7,201,790 B1
(45) Date of Patent: Apr. 10, 2007

(54) ZINC FLAKE COATING COMPOSITION

(76) Inventor: Ronald R. Savin, 12 Canyon Creek, Rancho Mirage, CA (US) 92270

( * ) Notice: Subject to any disclaimer, the term of this patent is extended or adjusted under 35 U.S.C. 154(b) by 45 days.

(21) Appl. No.: 11/293,886

(22) Filed: Dec. 2, 2005

(51) Int. Cl.
*A01N 25/10* (2006.01)
*A01N 59/16* (2006.01)
*C23F 11/00* (2006.01)
*C23F 11/18* (2006.01)

(52) U.S. Cl. .............................. 106/18.36; 106/14.05; 106/14.41; 106/14.44; 106/15.05; 427/385.5; 427/386; 523/177; 524/440

(58) Field of Classification Search ............. 106/14.05, 106/14.41, 14.44, 15.05, 18.36; 427/385.5, 427/386; 523/177; 524/440
See application file for complete search history.

(56) References Cited

U.S. PATENT DOCUMENTS 5,393,567 A * 2/1995 Wekenmann et al. .... 427/372.2

FOREIGN PATENT DOCUMENTS

| JP | 51-93934 A | * | 8/1976 |
| JP | 54-161642 A | * | 12/1979 |
| JP | 57-198767 A | * | 12/1982 |
| JP | 60-86160 A | * | 5/1985 |
| JP | 60-133072 A | * | 7/1985 |

* cited by examiner

*Primary Examiner*—Anthony J. Green
(74) *Attorney, Agent, or Firm*—Ladas and Parry LLP

(57) ABSTRACT

The present invention provides a coating composition comprising zinc particles and a binder wherein the zinc particles contain at least 80% by weight of zinc flake and wherein the zinc particle to binder weight ratio is between 2:1 to 9:1. The coating composition may be an anti-corrosive composition or an antifouling composition. The coating composition may also inhibit or galvanize rust formation. The coating composition is of particular use in the marine industry.

18 Claims, No Drawings

ZINC FLAKE COATING COMPOSITION

FIELD OF THE INVENTION

The present invention relates to a zinc flake rich coating composition. Particularly the invention relates to an improved coating composition which provides enhanced resistance to environmental attack on metallic and non metallic substrates and which can be applied by any conventional coating technique. Additionally the improved coating composition has been found to inhibit or galvanize rust formation. Furthermore the improved coating composition is also effective in preventing fouling and is of particular use in the marine industry.

BACKGROUND OF THE INVENTION

It is known to apply a coating to metallic substrates which are sensitive to corrosion, in order to protect them against environmental factors.

Examples of substrates requiring protection include hulls, interior and superstructures of ships, off-shore oil drilling platforms, metallic frames, bridges, automobile bodies and related equipment, storage tanks, guardrails and aircraft equipment. All these substrates, when insufficiently protected, undergo chemical transformation actions which are initially superficial but subsequently reduce their physical and particularly their mechanical characteristics, when they are exposed to severe natural or synthetic environmental conditions, such as heat, cold, ultraviolet radiation, moisture, particularly saline, wind, rain, sea water, snow, particle impacts and other harmful factors due to atmospheric pollution or to liquid or gaseous fluids resulting from the chemical, biochemical, biological and other industries.

Zinc-rich coatings containing zinc dust have been considered as the optimum anti-corrosion coatings on iron or steel substrates. However such coatings require an extremely high ratio of zinc dust to be effective and consequently their use has been restricted.

In the marine industry advances in antifouling coating technology are driven by environmental regulations and extended service requirements.

Fouling involves the formation of microbial biofilms and when these biofilms form on the hull of a vessel this may lead to increased drag and hence increased fuel consumption.

Coating compositions containing biocides such as tributyltin (TBT) compounds have been banned by the International Marine Organization (IMO) which leaves ablative copper coatings as those that are used primarily throughout the industry.

However, virtually all cuprous oxide coatings contain large amounts of copper to ensure the inhibition of fouling growth. These coatings typically include a rosin which causes the coating to leach such that a fresh surface of copper is exposed. This process continues until all of the copper has been leached after which a new coating must be applied. The ablated copper pollutes the world's ports, harms fish and impacts on the quality of the food chain.

Zinc flake, has been suggested for use in a number of anti-corrosion compositions. For example U.S. Pat. No. 5,338,348 discloses a coating composition for use in protecting metallic substrates from corrosion, comprising in weight percent, based on the total weight of the composition: from about 7% to 35% of film-forming substance for example a silicate, epoxy resin, vinyl chloride resin, polyurethane resin, acrylic or methacrylic ester polymer or an emulsion polymer; from about 35% to 55% of zinc powder; from about 5% to 25% of zinc flakes; from about 1% to 5% of at least one kind of amorphous silica; and up to about 30% particulate ferrophosphate whilst U.S. Pat. No. 5,334,631 describes a resin-based coating composition containing a mixture of zinc powder and zinc flake, epoxy resins being the preferred resins but polyesters, polyacrylates and polyurethanes being mentioned as possible alternatives.

The object of the present invention is to develop an effective environmentally safe improved coating composition and this has been achieved by providing a composition rich in zinc flake.

SUMMARY OF THE INVENTION

The present invention provides a coating composition comprising zinc particles and a binder wherein the zinc particles contain at least 80% by weight of zinc flake and wherein the zinc particle to binder weight ratio is between 2:1 to 9:1, preferably between 3:1 to 8:1 and advantageously between 4:1 to 6:1 e.g. 5:1.

The coating composition may be an antifouling composition or an anti-corrosive composition. The coating composition may also inhibit or galvanize rust formation.

The present invention also provides a method of preventing fouling of a substrate which comprises coating the substrate with the coating composition, a method of preventing corrosion of a metallic substrate which comprises coating the substrate with the coating composition and a method of inhibiting further rust formation on a substrate which comprises coating the rust formation with the coating composition.

DETAILED DESCRIPTION OF THE INVENTION

The zinc particles of the present invention are primarily zinc flakes. Zinc particles exist in three forms: powder, dust and flake. Zinc flake comprises a lamellar type structure and is typically produced from zinc dust by ball milling in a non-reactive fluid such as a hydrocarbon. The milling results in each dust particle being flattened into flake-like form.

The primary differences between the powder and dust on the one hand and flake on the other lie in their aspect ratio and their density. The aspect ratio of zinc flake (that is the ratio of diameter to thickness) is typically in the range of about 5:1 to 40:1, and preferably a range of about 15:1 to 25:1, more preferably about 20:1. Such flakes frequently have a thickness of from 0.5 to 2 microns, for example about 1 micron. Zinc powder on the other hand tends to spheroidal shaped particles having a particle size in the range 15 to 40 microns, whereas dust is also formed primarily of spheroidal particles of a size of from 3 to 15 microns. Zinc flake refers to particles having a particle size of 1 to 100 microns, preferably 6–50 microns, frequently in the range 10 to 15 microns as measured by a Coulter Particle Size Analyzer. Zinc dust has a tapped density above 3. Whereas zinc flake has a tapped density below 3, for example in the range 2 to 2.5, commonly about 2.4.

Zinc flake provides greater covering power and has lower density than zinc dust.

Typically the zinc particles for use in the present invention contain at least 80% by weight of zinc flake, preferably at least 90% by weight of zinc flake and advantageously at least 95% by weight zinc flake e.g. 100%.

The binder is usually an epoxy resin or other well known equivalents thereof including vinyl chloride resins, polyurethane resins and polyester resins.

Preferably the binder comprises an epoxy resin or a vinyl chloride resin.

Epoxy resins preferably contain at least one epoxy function per molecule and preferably have an epoxide value of 250 to 2500. Preferably the resins have an average molecular weight between 5,000 and 30,000.

Advantageously the binder may comprise a two component system which includes a curing agent.

Curing agents typically include at least one compound with an —$NH_2$, —$CONH_2$, NHR, —CONHR (wherein R is an alkyl group) and/or —COOH functional group, which react by way of these functional groups with the resin.

Preferably aliphatic or aromatic polyamides are used as curing agents, although aliphatic polyamines, aromatic polyamines, melamines, polyisocyanates or urea-formaldehyde resin may be used. The weight ratio of resin to curing agent preferably ranges from about 15:1 to about 3:1.

The resin is typically stored in an anhydrous solvent. The solvent may be an alcohol or a ketone e.g. methyl ethyl ketone. The solvent content is typically restricted to a maximum of about 8% by volume, in order to maintain the total volatile organic content (VOC).

Advantageously the coating composition includes between 1 to 10% by weight of amorphous or crystalline silica and advantageously between 4 to 9% by weight.

In a preferred embodiment of the invention the coating composition is non-ablative and typically contains less than 20% by weight of rosin, usually less than 10% by weight, and preferably less than 5% by weight of rosin. Advantageously the coating composition contains little to no rosin.

Preferably the only metallic component in the coating composition is zinc i.e the present invention advantageously provides a monometallic coating composition.

The present invention also provides a method of preventing fouling of a substrate which comprises coating said substrate with a composition as herein described above.

The substrate is usually any structure that spends an extensive period of time positioned in a body of water e.g. sea water. Typically the substrate is used in the marine industry and is usually the hull of a boat or a ship. The substrate may include port facilities and off-shore drilling platforms. The substrate may be formed from steel, fibreglass, aluminum or wood.

The present invention also provides a method of preventing corrosion which comprises coating a metallic substrate with a composition as herein described above. Typically the substrate may include hulls, interior and superstructures of ships, off-shore oil drilling platforms, metallic frames, bridges, automobile bodies and related equipment, storage tanks, guardrails, and aircraft equipment.

The present invention also provides a method of inhibiting further rust formation on a substrate which comprises coating the rust formation with a composition as herein described above.

The substrate comprising the rust formation may be any suitable metallic substrate.

The coating may be applied by brushing, rolling or spraying. Typically the thickness of the coating applied to the substrate is between 10–500 microns and usually between 50–150 microns e.g. 100 microns.

The invention will now be illustrated in the following examples.

EXAMPLE 1

Rust Inhibition

Compositions According to the Invention

The following coating compositions were formulated.

| Formula I (two component system) | |
|---|---|
| Parts by Weight | Ingredients |
| Part A | |
| 135 | Epoxy Resin[1] |
| 165 | Methyl ethyl ketone |
| 500 | Zinc flake[2] |
| 200 | Crystalline silica[3] |
| Part B | |
| 70 | Curing Agent[4] |
| 73 | Methyl ethyl ketone |

100 parts of A was added to 14.3 parts by weight of B to provide a composition according to the present invention.
[1]Resolution "EPON Resin 1001-X-75"
[2]Hyperseal "average particle size 12 microns, tapped density 2.2–2.4 kg/cm$^3$"
[3]Malvern Minerals "NOVACITE 337"
[4]Resolution "EPI-CURE Curing Agent 3115-X-70"

| Formula II | |
|---|---|
| Parts by Weight | Ingredients |
| 200 | Epoxy Ester[1] |
| 500 | Zinc flake[2] |
| 100 | Crystalline silica[3] |
| 200 | Methyl Ethyl Ketone |

[1]Accurez "Epi-Tex 183"
[2]Hyperseal "average particle size 12 microns, tapped density 2.2–2.4 kg/cm$^3$"
[3]Malvern Minerals "NOVACITE 337"

| Formula III | |
|---|---|
| Parts by Weight | Ingredients |
| 100 | Vinyl Resin[1] |
| 500 | Zinc flake[2] |
| 10 | Di iso dectyl phosphate |
| 390 | Methyl Ethyl Ketone |

[1]Dow Chemical "UCAR VAGH"
[2]Hyperseal "average particle size 12 microns, tapped density 2.2–2.4 kg/cm$^3$"

| Formula IV | |
|---|---|
| Parts by Weight | Ingredients |
| 250 | Epoxy Resin[1] |
| 500 | Zinc flake[2] |
| 100 | Crystalline silica[3] |
| 150 | Methyl Ethyl Ketone |

[1]Resolution "Epoxy GZ 488-N-40"
[2]Hyperseal "average particle size 12 microns, tapped density 2.2–2.4 kg/cm$^3$"
[3]Malvern Minerals "NOVACITE 337"

Formula V

| Parts by Weight | Ingredients |
| --- | --- |
| 250 | Epoxy Resin[1] |
| 500 | Zinc flake[2] |
| 15 | Amorphous silica[3] |
| 395 | Methyl Ethyl Ketone |

[1]Dow Chemical "DER 684-EK 40 epoxy"
[2]Hyperseal "average particle size 12 microns, tapped density 2.2–2.4 kg/cm³"
[3]Degussa "AEROSIL 972"

Comparative Compositions

The above compositions were reformulated wherein the zinc flake was replaced by aluminum.

Severely rusted panels were coated with the above compositions and exposed to a salt fog (ASTM B-117 test). After two months of exposure the severely rusted panels coated with the compositions according to the invention were unaffected whereas the panels coated with the comparative compositions completely rusted through with 72 hours.

EXAMPLE 2

Antifouling Performance

Composition According to the Invention

The ingredients listed below were blended together to form formulations A and B.

| Parts by Weight | Ingredients |
| --- | --- |
| Part A | |
| 135 | Epoxy Resin[1] |
| 185 | Methyl ethyl ketone |
| 80 | Tertiary butyl acetate |
| 100 | Crystalline silica[2] |
| 500 | Zinc flake[3] |
| 1000 | |
| Part B | |
| 70 | Curing agent[4] |
| 130 | Methyl ethyl ketone. |
| 200 | |

100 parts of A was mixed with 20 parts of B to provide an antifouling composition according to the present invention.
[1]Resolution "EPON Resin 1001-X-75"
[2]Malvern Minerals "NOVACITE 337"
[3]Hyperseal "average particle size 12 microns, tapped density 2.2–2.4 kg/cm³"
[4]Resolution "EPI-CURE Curing Agent 3115-X-70"

Comparative Composition 1

The above composition was reformulated wherein the zinc flake was replaced by zinc dust modified with 20% by weight zinc flake.

Comparative Composition 2

The ingredients listed below were blended together to provide an antifouling composition.

| Parts by Weight | Ingredients |
| --- | --- |
| 1440 | Cuprous Oxide |
| 215 | Vinyl Resin[1] |
| 55 | Rosin[2] |
| 165 | Methyl ethyl ketone |
| 115 | Tertiary Butyl Acetate |
| 5 | Amorphous silica[3] |

[1]Dow Chemical "UCAR VAGH"
[2]AKZO "Rosin Grade WW"
[3]Degussa "AEROSIL 972"

Panels coated with the composition according to the invention and the comparative compositions were immersed in San Diego Bay for approximately 6 months. After 6 months the panels were removed from the water. It was observed that the panels coated with the comparative examples were covered with slime and were ineffective in inhibiting fouling whereas the panel coated with the composition according to the present invention exhibited a surface covered with zinc salts, zinc oxide and zinc carbonate but exhibited no fouling.

The invention claimed is:

1. A method of preventing fouling of a substrate which comprises coating said substrate with a non ablative coating composition comprising zinc particles and a binder wherein the zinc particles contain at least 80% by weight of zinc flake and wherein the zinc particle to binder weight ratio is between 2:1 to 9:1, and placing said coated substrate in a body of water for an extended period of time, said body of water comprising microbes capable of forming a microbial biofilm on said substrate, said substrate comprising the coating composition at a thickness effective to inhibit formation on the substrate of the microbial biofilm over the extended period.

2. A method according to claim 1 wherein the substrate is the hull of a boat or a ship.

3. A method according to claim 2 wherein the substrate is formed from steel, fibreglass, aluminum or wood.

4. A method according to claim 1 wherein the zinc particle to binder ratio is between 3:1 to 8:1.

5. A method according to claim 1 wherein the zinc particle to binder ratio is between 4:1 to 6:1.

6. A method according to claim 1 wherein the zinc particles contain at least 90% by weight of zinc flake.

7. A method according to claim 1 wherein the zinc particles contain at least 95% by weight of zinc flake.

8. A method according to claim 1 wherein the binder comprises an epoxy resin or a vinyl chloride resin.

9. A method according to claim 1 wherein the binder comprises a two component system.

10. A method according to claim 1, wherein the coated substrate is not removed from the body of water for six months.

11. A method of inhibiting further rust formation on a substrate which comprises providing a substrate having a rust formation, and coating the rust formation with a coating composition comprising zinc particles and a binder wherein the zinc particles contain at least 80% by weight of zinc flake and wherein the zinc particle to binder weight ratio is between 2:1 to 9:1.

12. A method according to claim 11 wherein the substrate is selected from the group consisting of a hull, an interior of a ship, an off-shore oil drilling platform, a metallic frame, a bridge, an automobile body, a storage tank, a guardrail and aircraft equipment.

13. A method according to claim 11 wherein the zinc particle to binder ratio is between 3:1 to 8:1.

14. A method according to claim 11 wherein the zinc particle to binder ratio is between 4:1 to 6:1.

15. A method according to claim 11 wherein the zinc particles contain at least 90% by weight of zinc flake.

16. A method according to claim 11 wherein the zinc particles contain at least 95% by weight of zinc flake.

17. A method according to claim 11 wherein the binder comprises an epoxy resin or a vinyl-chloride resin.

18. A method according to claim 11 wherein the binder comprises a two component system.

* * * * *